(12) United States Patent
Jacobsen et al.

(10) Patent No.: US 7,206,639 B2
(45) Date of Patent: Apr. 17, 2007

(54) COCHLEAR DRUG DELIVERY SYSTEM AND METHOD

(75) Inventors: Stephen C. Jacobsen, Salt Lake City, UT (US); Tomasz J. Petelenz, Salt Lake City, UT (US)

(73) Assignee: Sarcos Investments LC, Salt Lake City, UT (US)

( * ) Notice: Subject to any disclaimer, the term of this patent is extended or adjusted under 35 U.S.C. 154(b) by 570 days.

(21) Appl. No.: 10/389,251

(22) Filed: Mar. 14, 2003

(65) Prior Publication Data

US 2003/0229336 A1 Dec. 11, 2003

Related U.S. Application Data

(60) Provisional application No. 60/364,431, filed on Mar. 15, 2002.

(51) Int. Cl.
*A61N 1/00* (2006.01)

(52) U.S. Cl. ........................................................ 607/57

(58) Field of Classification Search .................. 607/59, 607/890.1, 57; 604/2, 11, 21
See application file for complete search history.

(56) References Cited

U.S. PATENT DOCUMENTS

| | | | |
|---|---|---|---|
| 6,377,849 B1* | 4/2002 | Lenarz et al. .................. 604/21 |
| 6,685,697 B1* | 2/2004 | Arenberg et al. ........ 604/890.1 |
| 2003/0036783 A1* | 2/2003 | Bauhahn et al. .............. 607/59 |

* cited by examiner

*Primary Examiner*—George Manuel
(74) *Attorney, Agent, or Firm*—Thorpe North & Western LLP

(57) ABSTRACT

A drug administration system configured to administer a drug to a user's ear includes a housing, sized and shaped to substantially fit behind the user's ear, and configured to pump the drug in controlled amounts to the user's middle ear. A drug reservoir is disposed in the housing and includes a drug configured to treat an inner ear condition. A catheter is operatively coupled to the drug reservoir and is sized and shaped to extend from the drug administration unit into the user's middle ear.

59 Claims, 3 Drawing Sheets

COCHLEAR DRUG DELIVERY SYSTEM AND METHOD

This application claims the benefit of U.S. Provisional Patent Application No. 60/364,431, filed Mar. 15, 2002.

BACKGROUND OF THE INVENTION

1. Field of the Invention

The present invention relates generally to treatment of target disease areas of the body, including inner ear disorders, such as Meniere's disease, tinnitus, and hearing loss. More particularly, the present invention relates to a method and apparatus for administering medication to the disease target area, such as the middle ear and/or inner ear (or cochlea).

2. Related Art

Various situations or medical conditions of the inner ear require the administration of drugs or like medicines to the middle ear. Such medical conditions or inner ear disorders can include sudden neurosensory hearing loss, Meniere's disease, and tinnitus. These conditions affect up to 40 million persons in the United States, and are the cause of significant loss of productivity and quality of life. Costs to the U.S. military related to treatment of sudden neurosensory hearing loss are estimated at 1.5 billion dollars per year.

For example, Meniere's disease, also known as idiopathic endolymphatic hydrops, is classified as an inner ear disorder. Meniere's disease is characterized by episodic rotational vertigo (spinning sensation or dizziness), hearing loss, tinnitus (ringing, buzzing or roaring in the ears), and a sensation of pressure or fullness in the ear. The vertigo of Meniere's disease occurs in attacks of a spinning sensation, and is accompanied by dysequilibrium (an off-balance sensation), nausea, and vomiting. The vertigo lasts from 20 minutes to 2 hours (or more), during which the person is unable to perform normal activities.

Sudden neurosensory hearing loss, Meniere's disease, and tinnitus usually may be treated medically or surgically. Various medications may be taken in conjunction with a low salt diet. Such medications include urea, glycerol, isosorbide, diuretics (dyazide), acetazolamide (Diamox), steroids (prednisone or dexamethasone), antibiotics (gentamycin), calcium channel blockers (Fluanarizine or Cinnarzine), niacin, betahistine (Serc), or anesthetics.

One disadvantage with medications is that they are often administered orally or intravenously, each of which results in a systemic administration of the medication. Systemic administration of medication is problematic in some applications in that the medication is distributed throughout much of the patient's body. By distributing the medication throughout the patient's body, concentrations of the medication vary in different parts of the body. For instance, the concentration of the medication may be low in one area of the body but relatively high in other areas.

It is generally advantageous to treat a diseased portion of the body with a therapeutic concentration of the medication being administered, that is, a concentration high enough to effectively treat the condition but not so high as to reach a toxic level. However, it is often the case that systemic administration of medication is problematic in that the desired therapeutic level of medication is delivered to the diseased portion of the body that is being treated, but higher than therapeutic levels are delivered to other parts of the body. This can lead to the serious and undesirable result of systemic toxicity.

Surgical procedures used to treat these conditions include endolymphatic shunt, insertion of a Tympanostomy tube, sacculotomy, cochleosacculotomy, endolymphatic sac surgery, chemical labyrinthectomy with antibiotics, surgical labyrinthectomy, and vestibular nerve section surgery. The endolymphatic shunt procedure drains excess fluids from the inner ear. An incision is made behind the ear, through the mastoid, and a tube is inserted.

Insertion of a Tympanostomy tube is a minor procedure in which a tiny tube is inserted and maintained in a hole through the eardrum. Sacculotomy and cochleosacculotomy are also relatively minor procedures which involve perforation of the saccule through the stapes footplate (sacculotomy), or through the round window, via the basilar membrane (cochleosacculotomy).

Endolymphatic sac surgery includes: endolymphatic sac decompression, in which bone overlying the endolymphatic sac is drilled away to make a larger cavity for the sac; endolymph-subarachnoid shunt, which involves placing a tube between the endolymphatic sac and the cranium; endolymph-mastoid shunt, which involves placing a tube between the endolymphatic sac and the mastoid cavity; and endolymphatic sac ablation, which completely destroys the endolymphatic sac.

Chemical labyrinthectomy destroys the vestibular system, or vestibular hair cells, using certain antibiotics. Surgical labyrinthectomy is the surgical destruction of either a portion or the entire labyrinth. Finally, vestibular nerve section surgery cuts the nerve from the vestibular apparatus.

One disadvantage with surgical treatment is the expense and invasiveness of surgery. In addition, many of the surgical procedures used for treating these disorders are considered controversial.

SUMMARY OF THE INVENTION

It has been recognized that it would be advantageous to develop a system and method for treating diseased target areas of the body, including inner and/or middle ear disorders, such as sudden neurosensory hearing loss, Meniere's disease, and tinnitus. In addition, it would be advantageous to develop such a system and method for delivering drugs directly to the middle ear and cochlea and to diseased target areas in the head and neck area. In addition, it would be advantageous to develop such a system and method that is convenient, unobtrusive, and inexpensive.

The present invention provides a drug administration system configured to administer a drug to a user's ear, and includes a housing, sized and shaped to substantially fit behind the user's ear to pump the drug in controlled amounts to the user's middle ear. A drug reservoir can also be included and can be disposed in the housing and can include a drug configured to treat an inner ear condition. A catheter can be operatively coupled to the drug reservoir and can be sized and shaped to extend from the drug administration unit and into the user's middle ear.

In accordance with another aspect of the invention, the invention provides a drug administration system configured to administer a drug to a diseased target area of a user's body. The system can include a housing, sized and shaped to substantially fit behind the user's ear to pump the drug in controlled amounts to the diseased target area of the user's body. A drug reservoir can be disposed in the housing and can include a drug configured to treat the diseased target area. A catheter can be operatively coupled to the drug reservoir and can be sized and shaped to extend from the drug administration unit and into the user's body. The catheter can include a section at least partially disposed adjacent the diseased target area.

In accordance with another aspect of the invention, the invention provides a method for administering a drug to a user's ear, the method including the steps of: a) disposing a drug administration unit behind the user's ear, the drug administration unit including a drug reservoir containing a drug configured to treat an inner ear condition, and a catheter operatively coupled to the drug reservoir; b) disposing the catheter inside the user's ear; and c) dispensing the drug from the drug reservoir, through the catheter, and into the user's ear.

In accordance with another aspect of the invention, the invention provides a method for administering a drug to a diseased target area of a user's body, the method including the steps of: a) disposing a drug administration unit behind the user's ear, the drug administration unit including a drug reservoir containing a drug configured to treat the diseased target area, and a catheter operatively coupled to the drug reservoir; b) disposing at least a section of the catheter adjacent the diseased target area; and c) dispensing the drug from the drug reservoir, through the catheter, and to the diseased target area.

Additional features and advantages of the invention will be apparent from the detailed description which follows, taken in conjunction with the accompanying drawings, which together illustrate, by way of example, features of the invention.

DETAILED DESCRIPTION

Figure 1:
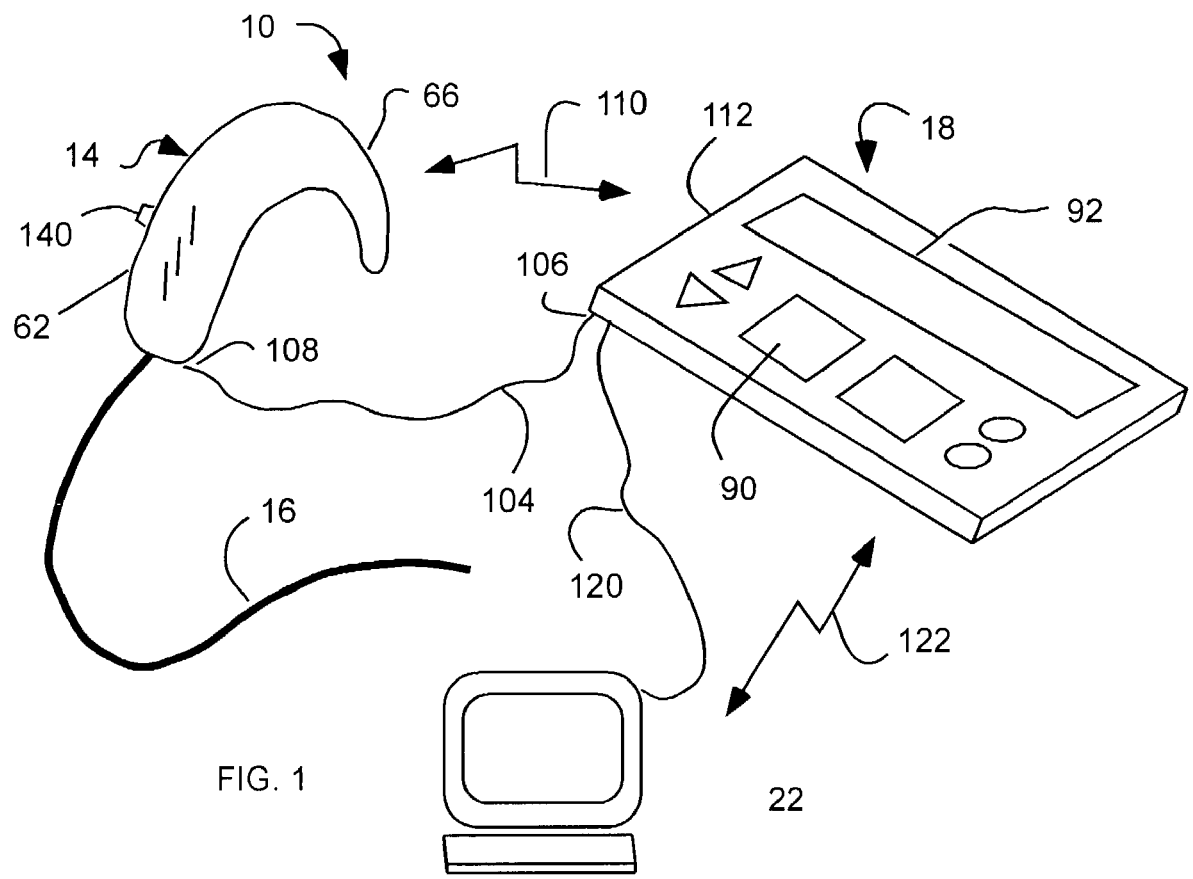
FIG. 1 is a schematic view of an embodiment of a drug delivery system in accordance with the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Figure 2:
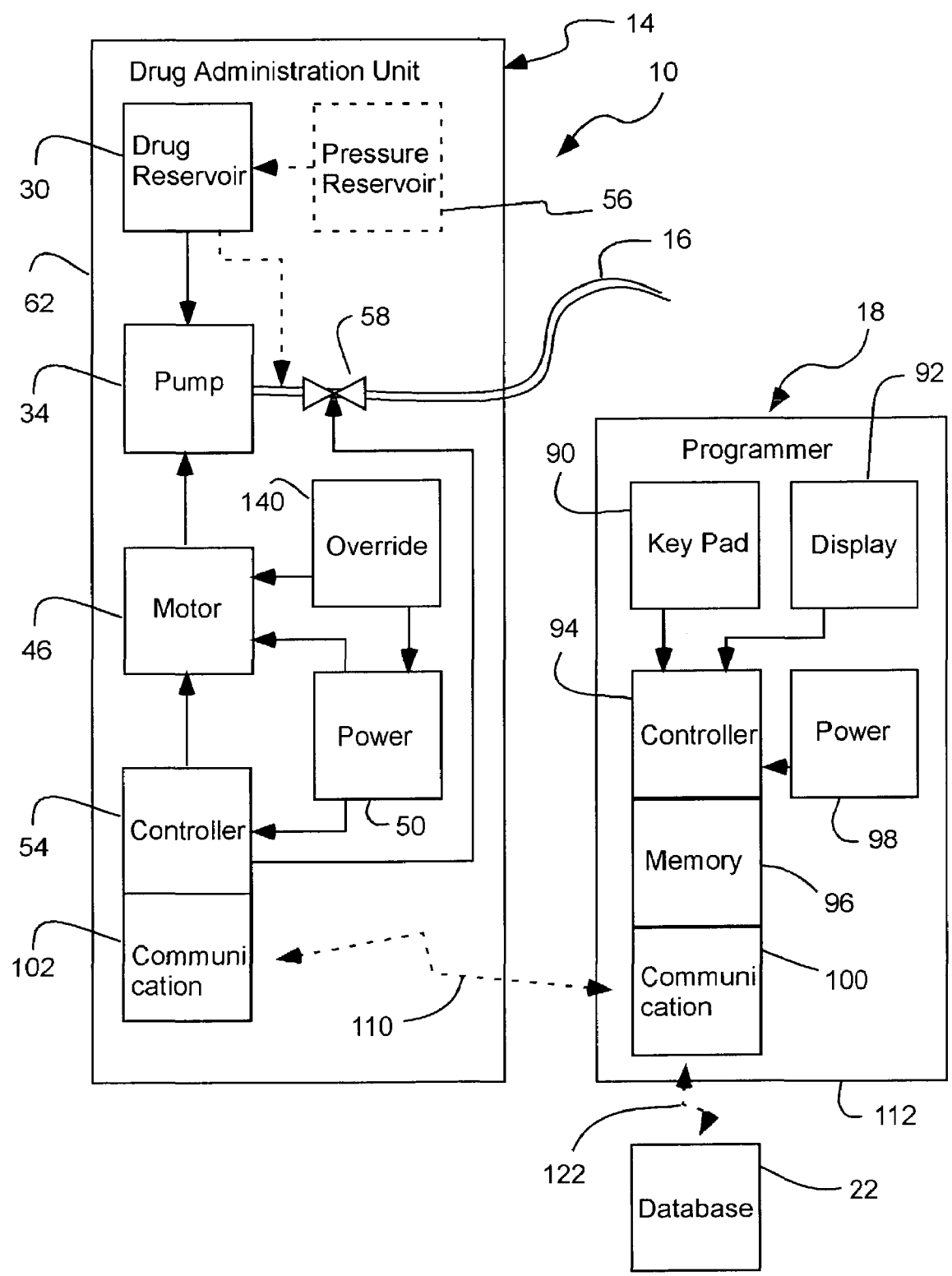
FIG. 2 is a schematic view of the drug delivery system of the present invention.

As illustrated in FIGS. 1 and 2, a drug administration system, indicated generally at 10, in accordance with the present invention is shown for administering a drug to a user's middle or inner ear, or the user's cochlea. The system 10 includes a drug administration unit 14, and a catheter 16 operatively or fluidly coupled to the drug administration unit 14 and extending to the user's middle ear. The system 10 also can include a separate programmer 18 and a database 22. Although the system and method of the present invention are described and illustrated with particular reference to treating Meniere's disease, it is of course understood that the system and method can be applied to other diseases or treatments. The drug administration unit 14 can be configured to pump any drug or medicament desired.

The drug administration unit 14 pumps a drug from a drug reservoir 30 to the user. The drug can be pumped by a pump 34 through the catheter 16 which can have a proximal end operatively or fluidly coupled to the pump 34. The catheter 16 can have a distal end inserted through the user's ear canal and ear drum, as discussed in greater detail below. Alternatively, the catheter can be inserted through the skin behind the outer ear and navigated into the middle ear. The drug can include gentamycin, steroids, gene vectors, apoptotic agents, regenerative agents, and the like.

The drug administration unit 14 also can include a controller 54 coupled to the driver or motor 46 to control the motor, and thus the pump 34. The controller 54 also can be electrically coupled to the power source 50. The controller 54 can include control electronics or circuitry, such as a microprocessor, and memory to store operating instructions and/or performance information, as is known in the art. A driver or motor 46 can be connected to drive the pump 34. A power source 50, such as a battery, can be connected to power the motor 46, and thus the pump 34.

Alternatively, the drug administration unit 10 can include a pressure reservoir 56 operatively coupled to the drug reservoir 30 to drive or expel the drug out of the drug reservoir 30. For example, the pressure reservoir 56 can include a gas or fluid under pressure, and can bear against the drug reservoir 30, such as through a diaphragm. Alternatively, the drug reservoir itself can be pressurized, in which case a dosing valve can be disposed between the pressurized reservoir and the catheter. Of course, a dosing valve can also be utilized in those embodiments that do not include a pressurized reservoir.

The motor 46 and pressure reservoir 30 are examples of a means for pumping, forcing, dispelling and/or dispensing the drug from the drug reservoir. It is of course understood that other means can be used, including for example, mechanical springs exerting a force against the drug reservoir, an electric motor, a spring wound motor, a chemical reaction source creating a pressure, etc.

In addition, the drug administration unit 10 can include a control valve 58 operatively coupled to the drug reservoir 30, the pump 34, or the catheter 16. The control valve 58 can control the rate of drug delivery. The controller 54 can be operatively coupled to the control valve 58 to control the valve, and thus the delivery of the drug.

The drug administration unit 14 can include a housing 62 which houses the reservoir 30, the pump 34, the motor 46 (or pressure reservoir 56), the power source 50, the controller 54 and the control valve 58. In one aspect, the drug administration unit 14 or the housing 62 is sized to be relatively small, and thus can be inconspicuous.

Figure 3:
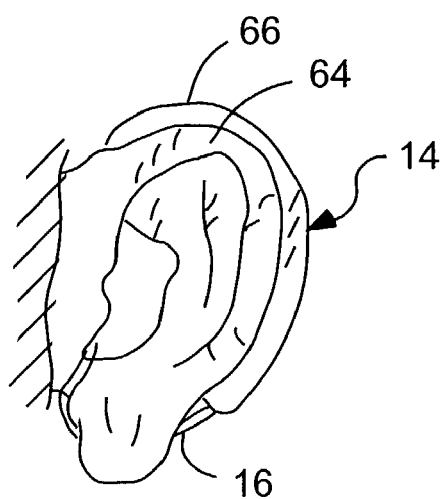
FIG. 3 is a side view of an embodiment of a drug administration unit in accordance with the present invention disposed behind a user's ear.
Figure 5:
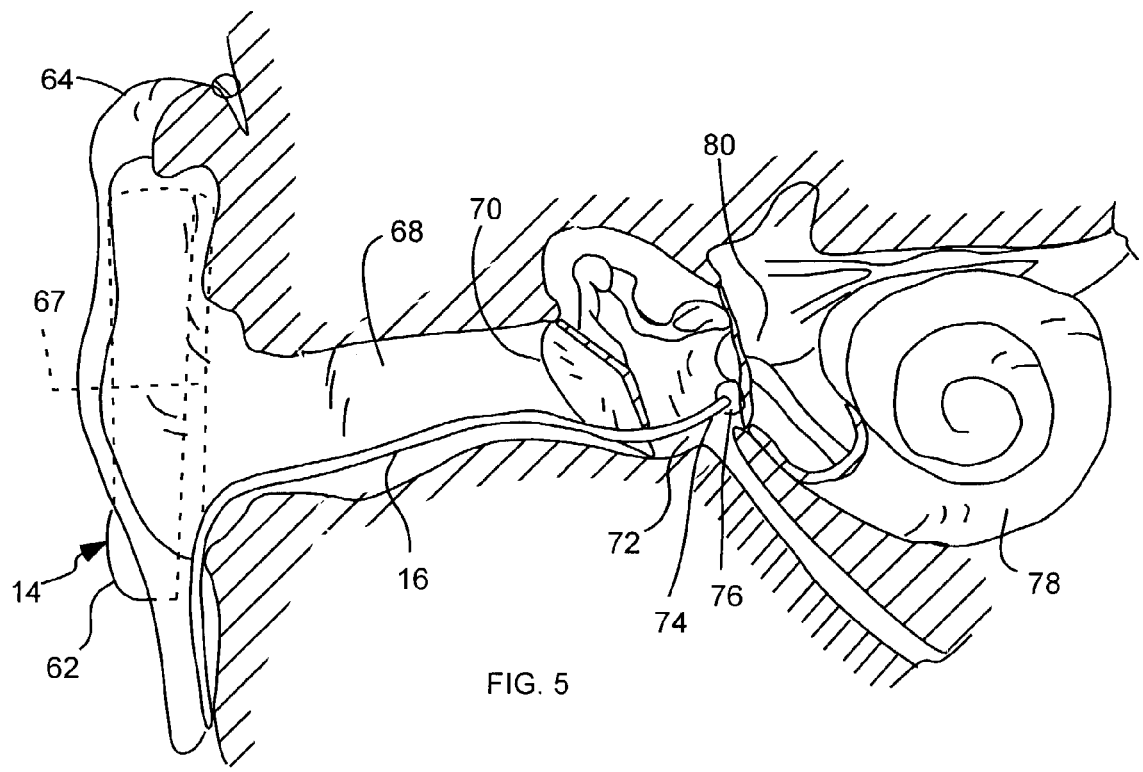
FIG. 5 is a cross-sectional view of a user's ear with a catheter in accordance with an embodiment of the drug delivery system.

Referring to FIGS. 3 and 5, the housing 62 can be shaped, sized, and configured to substantially fit behind the user's ear 64. Thus, the housing 62 can be substantially unnoticeable behind the user's ear 64, or can be concealed behind the user's ear. The housing 62, or drug administration unit 14, can have a teardrop shape, or lima bean shape, as shown, to conform to the contours of the user's ear, and help conceal the housing 62 behind the user's ear 64. In one aspect, a majority of the housing 62 is hidden by the user's ear 64. An inconspicuous housing 62 or drug administration unit 14 can have a distinct advantage over larger, more conspicuous drug pumps, especially for younger users who are particularly concerned with appearance and being accepted by peers.

The drug administration unit 14 advantageously can be directly attached to the user's ear 64 or head. Referring to FIGS. 1 and 3, the drug administration unit 14 has an arcuate earpiece 66 extending from the housing 62 and which is sized and shaped to extend over the user's ear 64, or over an attachment between the user's ear and the user's head, to secure the drug administration unit 14 behind the user's ear 64. The earpiece 66 may be a separate member attached to the housing 62, or may be formed integrally with the housing 62. Alternatively, an adhesive pad 67 (FIG. 5) can be disposed on the housing 62 to adhere the housing 62 to the user's skin behind the ear. An earpiece or an adhesive pad are examples of attachment means for attaching the housing 62 or drug administration unit 14 behind the user's ear 64. It is of course understood that any means for attaching may be used, including for example, a ring fitting around the user's ear, a portion of the user's eye glasses, etc.

As indicated above, the catheter 16 is operatively or fluidly coupled to the drug administration unit 14. A first or proximal end of the catheter 16 can be operatively or fluidly coupled to the pump 34 or drug reservoir 30, while a second or distal end can be disposed in the user's middle ear. The catheter 16 can be coupled to the housing 62 opposite the ear piece 66, and sized and shaped to extend under the user's ear 64 (such as between the ear lobe and head) and into the ear 64, as shown in FIGS. 3 and 5. Referring to FIG. 5, the catheter 16 can be sized and shaped to extend through the user's ear canal 68 and ear drum 70, and into the user's middle ear 72.

Thus, in one embodiment, the catheter 70 has a length less than approximately 10 cm. However, in alternative embodiments the catheter can be of any length. For instance, the present invention can be used to deliver medication to target areas other than the ear near which the system is disposed. Such target areas can include head, neck, eyes, nose, throat, the contralateral ear, etc. Of course, utilizing the system for treatment of various diseased target areas may require a variety of catheter lengths to adequately reach the target area while the drug delivery system is held relatively motionless behind the user's ear. The system can be advantageously used in these applications to provide the patient with mobility while remaining substantially concealed behind the ear. In this embodiment, the patient is provided with a greater level of mobility than conventional methods and relative movement between features of the drug delivery system is reduced to a minimum.

In one aspect, a distal end 74 of the catheter 16 is configured to be disposed in the middle ear 72, adjacent the circular window 76 of the cannula 78. Thus, the catheter 16 may deliver the drug to the cannula 78. Alternatively, the distal end 74 of the catheter 16 may be configured to deliver a drug to other locations in the middle ear 72 or inner ear 80. In addition, in one embodiment the drug administration unit can be implanted under the patient's skin.

Figure 6:
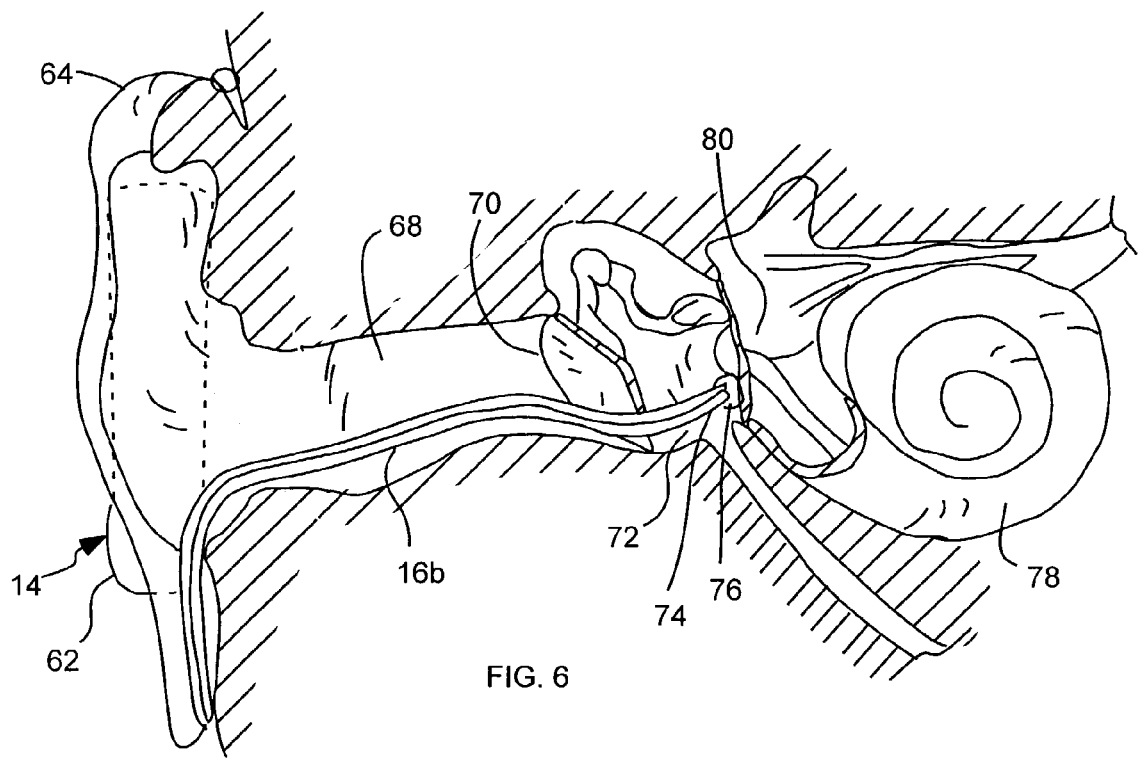
FIG. 6 is a cross-sectional view of a user's ear with another catheter in accordance with an embodiment of the present invention.

In addition, referring to FIG. 6, a catheter 16b can be configured to circulate the drug to maintain a constant concentration of the drug at the distal end 74, and thus at the circular window 76. The catheter 16b may form a loop with a distal end of the loop disposed at the round window. Thus, the catheter 16b can include two hollows or lumens, one for delivery and one for return. In the embodiment just described, the catheter includes a "closed loop" catheter which includes means for circulating the drug between the catheter and various components of the drug delivery system. In addition, the catheter can also include any type of catheter known in the art. Thus, as used herein, the term "closed loop" shall be understood to include systems that provide for circulation of the drug being delivered between the catheter and various components of the drug delivery system. A conventional catheter can also be used, wherein the catheter may terminate in a membrane which serves to deliver the medication at a controlled rate, but does not include a path for otherwise returning or circulating the medication.

The drug reservoir 30 can be sized to contain approximately a one-month supply of the drug. In addition, the entire drug administration unit 14 can be designed to be disposable after the drug supply is depleted, or after about a month. It is anticipated that the entire drug administration unit 14 and catheter 16 can be removed and disposed.

Alternatively, the pump 34 and reservoir 30 can be removably disposed in the drug administration unit 14 or housing 62, and can be removed and disposed after use. Similarly, the catheter 16 also can be removed and disposed. A new reservoir 30, pump 34, and catheter 16 can then be disposed in the drug administration unit 14. Thus, any component that has fluid contact with the user's body can be disposed of after use. The motor 46, power source 50, controller 54, and/or housing 62 can be reusable. Thus, the reservoir 30 and pump 34 are disposable for health reasons, while the motor 46, power source, and controller 54 can be reusable for cost effectiveness. Similarly, the pressure reservoir 56 can be removably disposed in the housing 62, and can be replaceable as required.

As indicated above, the drug administration unit 14 and housing 62 can be small and inconspicuous. Thus, the pump 34 itself can be relatively small. For example, the pump 34 may have a stroke volume of 1 µl (microliter). In addition, the pump 34 should be accurate (1% to 5%) and reliable. In one embodiment, the pump 34 can have a dose range of 1–100 µl/hr, while in other embodiments, the dose range can be above or below this range.

The pump 34 can be a micromotor-driven, micropiston pump, as described in U.S. Pat. Nos. 5,944,495; 5,941,533; 5,931,647; 5,799,690; 5,710,401; 5,647,575; 5,632,606; 5,618,163; 5,603,354; and 5,556,263, which are herein incorporated by reference.

The programmer or control unit 18 advantageously can be physically separate from the drug administration unit 14, thus further reducing the size of the drug administration unit 14. The programmer 18 can control, or provide the operating instructions, to the drug administration unit 14, or controller 54 thereof. Thus, although physically separated, the programmer 18 and drug administration unit 14 can be operatively coupled, or can be in communication, as described in greater detail below.

The programmer 18 can include a manual input device 90, such as a keypad, to receive manual instructions from a user. The programmer 18 also can include a visual display 92 to display information. In one aspect, the programmer 18 can include a programmer controller 94 for calculating or determining a drug dose, and appropriate operating instructions for the drug administration unit 14 to achieve the calculated dose. Memory 96 can be connected to the programmer controller 94 to store the operating instructions for the drug administration unit 14, and any performance information from the drug administration unit 14. A power source 98, such as a battery, can be connected to the programmer controller 94.

The programmer 18 can be controlled with a variety of control units. For instance, the control unit may be comprised of a PDA or similar device which provides integration and communication between the programmer and various components of the drug administration unit. Utilizing a PDA or similar device can enable the programmer to be controlled by the user, and can be tailored to various levels of user sophistication. Of course, any suitable programmer can be used with the present invention. In addition, the PDA itself can be used as a programmer.

As indicated above, the programmer 18 and drug administration unit 14 can be operatively coupled, or can be in communication, so that operating instructions determined by the programmer 18, or programmer controller 94, can be communicated or transferred to the drug administration unit 14, or controller 54. Thus, the programmer 18 and drug administration unit 14 can include communication devices 100 and 102, respectively, configured to transmit and/or receive information. The programmer 18 and drug administration unit 14 can be electrically coupled by an electronic cable 104, which is removably connected to respective data ports 106 and 108. Thus, the operating instructions from the programmer controller 94 can be transmitted by the cable 104 to the controller 54. Alternatively, the programmer 18 and drug administration unit 14 can communicate wirelessly, or utilize wireless communications. For example, the communication devices 100 and 102 can be wireless, or can include transmitter/receivers for transmitting and/or receiving radio frequencies (RF), acoustic waves, or infrared (IR), indicated by 110. In addition, performance information from the drug administration unit 14 can also be transmitted to the programmer 18.

The cable 104 or transmitter/receivers are examples of means for operatively coupling the programmer 18 and the drug administration unit 14 or controller 54, and for transferring instructions from the programmer to the controller, or to and from the controller 94 or memory 96 of the programmer and the controller 54 or memory of the drug administration unit. In addition, performance information can be transferred from the drug administration unit 14 to the programmer 18. It is of course understood that any means for transferring may be utilized, including for example, any type of electromagnetic radiation, vibrations, magnetism, etc.

As indicated above, the separate programmer 18 allows certain components, such as the input device 90, display 92, programmer controller 94, etc., to be physically separated from the drug administration unit 14 so that the drug administration unit 14 can be as small as possible, and thus easy to conceal. In addition, the separate programmer 18 allows important operating or control components, such as the input device 90, to be removed from the drug administration unit 14 to prevent tampering, such as may happen with a younger user.

The programmer 18 also includes a housing 112 which houses the input device 90, display 92, programmer controller 94, power supply 98, memory 96, and communication device 100. The input device 90 can include one or more push-type buttons for receiving input or instructions in response to prompts on the display 92. Alternatively, the display 92 and input device 90 may be integrated to form touch-screen-type display and input.

In one aspect, the programmer 18, or memory 96, stores or records the dose information, such as time and date, and drug dose. Furthermore, a record of several entries of drug dose for different dates and times preferably are recorded. These records may then be downloaded to a database 22, such as in a computer, for further analysis by the user, doctor, or healthcare professional. As described above, the records in the memory 96 may be transferred over an electric cable 120, or RF or IR transmission, indicated by 122. Thus, the records can be sent via phone-line or remotely. The records allow the doctor or healthcare professional determine whether adjustments need to be made in the drug doses, etc.

Figure 4:
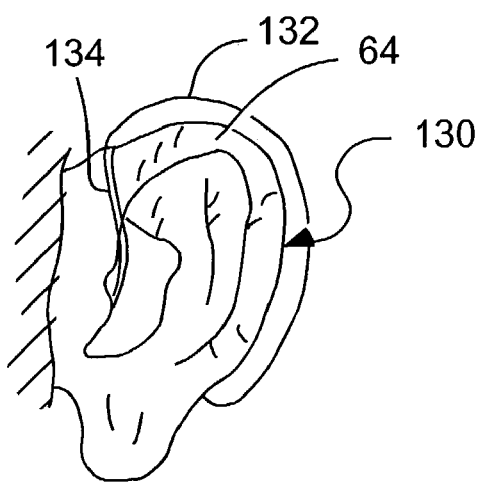
FIG. 4 is a side view of another embodiment of a drug administration unit in accordance with the present invention disposed behind a user's ear.

Referring to FIG. 4, another drug administration unit 130 is shown which is similar in many respects to that described above. The unit 130 includes an arcuate earpiece 132 for securing the unit 130 to the user's ear 64. A catheter 134 extends along the earpiece 132 and into the user's ear 64. The catheter 134 can be partially disposed within the earpiece 132, or can be disposed externally of the earpiece 132. In addition, the catheter 134 can have a rigid portion which itself forms the earpiece 132.

Referring again to FIG. 1, the drug administration unit 14 can have a manual input device, such as buttons 140, to act as emergency override controls. Thus, the buttons 140 can be electrically coupled to the motor controller 54 and/or power source 50 to stop operation of the motor 46, and thus the pump 34.

A method for using the above-described system, and for administering a drug to a user's ear, includes disposing the drug administration unit behind the user's ear, and disposing the catheter inside the user's ear. For example, an arcuate earpiece can be disposed over the user's ear, and a distal end of the catheter can be disposed through the user's eardrum. The drug can be dispensed from the drug reservoir, through the catheter, and into the user's ear. The drug can be dispensed by pumping the drug from the drug reservoir with a pump disposed in the housing and operatively coupled to the drug reservoir. Alternatively, the drug can be dispensed by forcing the drug from the drug reservoir with a pressure reservoir disposed in the housing and operatively coupled to the drug reservoir.

Operating instructions can be provided to the drug administration unit from a programmer that can be physically separate from the drug administration unit. The drug can be controlled with a control valve operatively coupled between the drug reservoir and the catheter. Drug delivery information can be obtained from the drug administration unit, and stored in a database.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A drug administration system configured to administer a drug to a user's ear, the system comprising:
    a) a housing, sized and shaped to substantially fit behind the user's ear, and having means for pumping the drug in controlled amounts to the user's middle ear, wherein the means for pumping includes a motor and pressure reservoir;
    b) a drug reservoir, disposed in the housing, including a drug configured to treat an inner ear condition; and
    c) a catheter, operatively coupled to the drug reservoir, sized and shaped to extend from the drug administration unit and into the user's middle ear, wherein the catheter includes a closed loop with a portion of the closed loop configured to be disposed in the user's middle ear.

2. A system in accordance with claim 1, further comprising a pump, disposed in the housing and operatively coupled to the drug reservoir, to pump the drug from the reservoir through the catheter.

3. A system in accordance with claim 2, wherein the catheter is configured to be disposed in the user's middle ear.

4. A system in accordance with claim 2, further comprising:
   a) a controller, disposed adjacent the pump and operatively coupled to the drug reservoir, to control administration of the drug;
   b) a programmer, separate from the housing, to provide operating instructions to the controller; and
   c) communication means, associated with the controller and programmer, for operatively coupling the controller and programmer and for transferring instructions from the programmer to the controller.

5. A system in accordance with claim 1, further comprising a pump, implantable under the user's skin and operatively coupled to the drug reservoir, to pump the drug from the reservoir through the catheter.

6. A system in accordance with 1, wherein the catheter extends from the drug administration unit, through the user's outer ear and ear drum, and into the user's middle ear.

7. A system in accordance with claim 1, wherein the catheter is at least partially implanted under the user's skin.

8. A system in accordance with claim 1, further comprising the pressure reservoir, disposed in the housing and operatively coupled to the drug reservoir, to force the drug from the reservoir through the catheter.

9. A system in accordance with claim 1, further comprising a control valve, operatively coupled between the drug reservoir and the catheter, to control flow of the drug.

10. A system in accordance with claim 1, wherein the catheter is less than approximately 10 cm long.

11. A system in accordance with claim 1, wherein the housing includes a curvature configured to conform to the user's ear.

12. A system in accordance with claim 1, further comprising an arcuate earpiece, attached to and extending from the drug administration unit, and sized and shaped to extend over the user's ear to secure the drug administration unit behind the user's ear.

13. A system in accordance with claim 12, wherein the catheter extends along the earpiece and into the user's ear canal.

14. A system in accordance with claim 1, wherein the drug reservoir is removably disposed in the housing.

15. A system in accordance with claim 1, wherein the drug reservoir is disposed outside the housing.

16. A system in accordance with claim 1, further comprising:
   a) a controller, disposed in the housing and operatively coupled to the drug reservoir, to control administration of the drug;
   b) a programmer, separate from the housing, to provide operating instructions to the controller; and
   c) communication means, associated with the controller and programmer, for operatively coupling the controller and programmer and for transferring instructions from the programmer to the controller.

17. A method for administering a drug to a user's ear, comprising the steps of:
   a) disposing a drug administration unit behind the user's ear, the drug administration unit including a drug reservoir containing a drug configured to treat an inner ear condition, and a catheter operatively coupled to the drug reservoir;
   b) disposing the catheter inside the user's ear, wherein the catheter includes a closed loop with a portion of the closed loop configured to be disposed in the user's ear; and
   c) circulating the drug from the drug reservoir, through a catheter, and into the user's ear, to maintain a constant concentration of the drug at a distal end of the catheter, wherein the step of circulating further comprises circulating the drug into and out of the user's ear with the catheter.

18. A method in accordance with claim 17, wherein the step of disposing the catheter further comprises the step of disposing the distal end of the catheter through the user's ear drum.

19. A method in accordance with claim 17, wherein the step of disposing the catheter inside the user's ear includes the step of disposing the catheter inside an ear contralateral to the ear behind which the drug administration unit is disposed.

20. A method in accordance with claim 17, wherein the step of disposing the catheter further comprises the step of implanting the catheter under the user's skin.

21. A method in accordance with claim 20, wherein the step of disposing the catheter further comprises the step of inserting the catheter through the user's skin in an insertion location located substantially behind the user's ear.

22. A method in accordance with claim 17, further comprising the step of providing operating instructions to the drug administration unit from a programmer that is physically separate from the drug administration unit.

23. A method in accordance with claim 17, wherein the step of circulating further comprises the step of pumping the drug from the drug reservoir with a pump operatively coupled to the drug reservoir.

24. A method in accordance with claim 23, wherein the pump is implanted under the user's skin.

25. A method in accordance with claim 23, wherein the pump is disposed within the housing.

26. A method in accordance with claim 23, further comprising the step of providing operating instructions to the drug administration unit from a control unit disposed on the pump.

27. A method in accordance with claim 17, wherein the step of circulating further comprises the step of forcing the drug from the drug reservoir with a pressure reservoir disposed in the housing and operatively coupled to the drug reservoir.

28. A method in accordance with claim 17, wherein the step of circulating further comprises the step of controlling the drug with a control valve operatively coupled between the drug reservoir and the catheter.

29. A method in accordance with claim 17, wherein the step of circulating further comprises the step of delivering the drug into the user's ear with a catheter disposed in the user's ear.

30. A method in accordance with claim 17, wherein the step of disposing the drug administration unit behind the user's ear further comprises the step of disposing an arcuate earpiece attached to the drug administration unit over the user's ear.

31. A method in accordance with claim 17, further comprising the steps of:
  a) removing the drug reservoir from the drug administration unit; and
  b) providing a new drug reservoir to the drug administration unit.

32. A method in accordance with claim 17, further comprising the steps of:
  a) obtaining drug delivery information from the drug administration unit; and
  b) storing the drug delivery information in a database.

33. A drug administration system configured to administer a drug to a diseased target area of a user's body, the system comprising:
  a) a housing, sized and shaped to substantially fit behind the user's ear, having a means for pumping the drug in controlled amounts to the diseased target area of the user's body, wherein the means for pumping includes a motor and pressure reservoir;
  b) a drug reservoir, disposed in the housing, including a drug configured to treat the diseased target area; and
  c) a catheter, operatively coupled to the drug reservoir, sized and shaped to extend from the drug administration unit and into the user's body, the catheter including a closed loop with a portion of the closed loop configured to be disposed adjacent the diseased target area.

34. A system as in claim 33, wherein the diseased target area of the user's body are organs of the user's head and neck selected from the group consisting of: external and internal organs.

35. A system as in claim 33, wherein the diseased target area of the user's body is selected from the group consisting of the user's: head, neck, brain, eye, ear, throat and nose.

36. A system in accordance with claim 33, further comprising a pump, disposed in the housing and operatively coupled to the drug reservoir, to pump the drug from the reservoir through the catheter.

37. A system in accordance with claim 33, further comprising a pump, implantable under the user's skin and operatively coupled to the drug reservoir, to pump the drug from the reservoir through the catheter.

38. A system in accordance with claim 37, further comprising:
  a) a controller, disposed adjacent the pump and operatively coupled to the drug reservoir, to control administration of the drug;
  b) a programmer, separate from the housing, to provide operating instructions to the controller; and
  c) communication means, associated with the controller and programmer, for operatively coupling the controller and programmer and for transferring instructions from the programmer to the controller.

39. A system in accordance with claim 33, wherein the catheter is at least partially implanted under the user's skin.

40. A system in accordance with claim 33, wherein the pressure reservoir is disposed in the housing and operatively coupled to the drug reservoir, to force the drug from the reservoir through the catheter.

41. A system in accordance with claim 33, further comprising a control valve, operatively coupled between the drug reservoir and the catheter, to control flow of the drug.

42. A system in accordance with claim 33, wherein the housing includes a curvature configured to conform to the user's ear.

43. A system in accordance with claim 33, wherein the catheter includes a portion configured to be disposed adjacent the diseased target area.

44. A system in accordance with claim 33, further comprising an arcuate earpiece, attached to and extending from the drug administration unit, and sized and shaped to extend over the user's ear to secure the drug administration unit behind the user's ear.

45. A system in accordance with claim 33, wherein the drug reservoir is removably disposed in the housing.

46. A system in accordance with claim 33, wherein the drug reservoir is disposed outside the housing.

47. A system in accordance with claim 33, further comprising:
  a) a controller, disposed in the housing and operatively coupled to the drug reservoir, to control administration of the drug;
  b) a programmer, separate from the housing, to provide operating instructions to the controller; and
  c) communication means, associated with the controller and programmer, for operatively coupling the controller and programmer and for transferring instructions from the programmer to the controller.

48. A method for administering a drug to a diseased target area of a user's body, comprising the steps of:
  a) disposing a drug administration unit behind the user's ear, the drug administration unit including a drug reservoir containing a drug configured to treat the diseased target area, and a catheter operatively coupled to the drug reservoir, the catheter having a closed loop with a portion of the closed loop being disposed adjacent the diseased target area;
  b) disposing at least a section of the catheter adjacent the diseased target area; and
  c) circulating the drug from the drug reservoir, through the catheter to the diseased target area, to maintain a constant concentration of the drug at a the diseased target area, wherein the step of circulating further comprises circulating the drug with the catheter having the closed loop.

49. A method in accordance with claim 48, wherein the step of disposing the catheter further comprises the step of implanting the catheter under the user's skin.

50. A method in accordance with claim 48, further comprising the step of providing operating instructions to the drug administration unit from a programmer that is physically separate from the drug administration unit.

51. A method in accordance with claim 48, wherein the step of circulating further comprises the step of pumping the drug from the drug reservoir with a pump operatively coupled to the drug reservoir.

52. A method in accordance with claim 51, wherein the pump is implanted under the user's skin.

53. A method in accordance with claim 51, further comprising the step of providing operating instructions to the drug administration unit from a control unit disposed on the pump.

54. A method in accordance with claim 48, wherein the step of circulating further comprises the step of forcing the drug from the drug reservoir with a pressure reservoir disposed in the housing and operatively coupled to the drug reservoir.

55. A method in accordance with claim 48, wherein the step of circulating further comprises the step of controlling the drug with a control valve operatively coupled between the drug reservoir and the catheter.

56. A method in accordance with claim 48, wherein the step of circulating further comprises the step of delivering the drug with a catheter disposed adjacent the diseased target area.

57. A method in accordance with claim 48, wherein the step of disposing the drug administration unit behind the user's ear further comprises the step of disposing an arcuate earpiece attached to the drug administration unit over the user's ear.

58. A method in accordance with claim 48, further comprising the steps of:
   a) removing the drug reservoir from the drug administration unit; and
   b) providing a new drug reservoir to the drug administration unit.

59. A method in accordance with claim 48, further comprising the steps of:
   a) obtaining drug delivery information from the drug administration unit; and
   b) storing the drug delivery information in a database.

* * * * *